United States Patent [19]
Kressel et al.

[11] Patent Number: 5,307,814
[45] Date of Patent: May 3, 1994

[54] EXTERNALLY MOVEABLE INTRACAVITY PROBE FOR MRI IMAGING AND SPECTROSCOPY

[75] Inventors: Herbert Y. Kressel, Wynnesal; Edward J. Rhinehart, Monroeville; Mitchell Schnall, Lansdowne; Robert E. Lenkinski, Drexel Hill, all of Pa.; Yutaka Imai, Tokyo, Japan

[73] Assignees: Medrad, Inc., Pittsburgh; The Trustees of the University of Pennsylvania, Philadelphia, both of Pa.

[21] Appl. No.: 760,463

[22] Filed: Sep. 17, 1991

[51] Int. Cl.$^5$ .................. A61B 5/055; A61M 25/10
[52] U.S. Cl. .................. 128/653.5; 128/772; 606/192; 606/194; 604/96; 604/104
[58] Field of Search .......... 128/653.2, 653.5, 778, 128/657, 772, 786; 606/191–194, 197; 604/55, 96, 104

[56] References Cited

U.S. PATENT DOCUMENTS

| | | | |
|---|---|---|---|
| 2,085,644 | 6/1937 | Ferciot | 128/407 |
| 2,126,257 | 8/1938 | Hird | 128/303.11 |
| 4,276,874 | 7/1981 | Wolvek et al. | 604/96 |
| 4,338,942 | 7/1982 | Fogarty | 604/99 |
| 4,764,726 | 8/1988 | Misic et al. | 324/322 |
| 4,775,371 | 10/1988 | Mueller, Jr. | 604/103 |
| 4,793,351 | 12/1988 | Landman et al. | 128/344 |
| 4,886,506 | 12/1989 | Lovgren et al. | 604/280 |
| 4,911,163 | 3/1990 | Fina | 606/127 |
| 4,917,102 | 4/1990 | Miller et al. | 128/657 |
| 4,920,318 | 4/1990 | Misic et al. | 324/318 |
| 4,943,275 | 7/1990 | Stricker | 604/96 |
| 4,960,106 | 10/1990 | Kubokawa et al. | 128/6 |
| 4,989,608 | 2/1991 | Ratner | 128/653 A |
| 5,035,231 | 7/1991 | Kubokawa et al. | 128/653.5 |
| 5,050,607 | 9/1991 | Bradley et al. | 128/653 A |
| 5,071,406 | 12/1991 | Jang | 604/96 |
| 5,090,957 | 2/1992 | Moutafis et al. | 604/96 |
| 5,104,377 | 4/1992 | Levine | 604/55 |
| 5,108,370 | 4/1992 | Walinsky | 604/96 |
| 5,116,305 | 5/1992 | Milder et al. | 604/96 |

FOREIGN PATENT DOCUMENTS

| | | | |
|---|---|---|---|
| 0385367 | 9/1990 | European Pat. Off. | 128/653.5 |
| 61-90525 | 5/1986 | Japan . | |
| 62-286451 | 12/1987 | Japan . | |
| 63-49150 | 3/1988 | Japan . | |
| 63-270036 | 11/1988 | Japan . | |
| 1-20832 | 1/1989 | Japan . | |

*Primary Examiner*—Lee S. Cohen
*Assistant Examiner*—K. M. Pfaffle
*Attorney, Agent, or Firm*—Keck, Mahin & Cate

[57] ABSTRACT

An insertable intracavity probe for use in magnetic resonance imaging of an area of interest in a body cavity particularly the colon, has an elongate shaft with a handle at its proximal end and an inflatable balloon structure at its distal end. The balloon structure has an outer balloon containing a loop-type pickup coil for connection to an interfacing network. The coil is sandwiched between two internal separately inflatable balloons, and when the probe is inserted, the coil can be optimally positioned relative to the area of interest by controlled differential inflation of the balloons. The probe also has an insertable rod-like mandrel for providing twisting orbital-type movement of the balloon structure on the shaft, by rotation of the mandrel, useful to steer the probe along curves or bends in the body cavity when it is being inserted. In a modified form of the probe, the mandrel can be used to rotate the coil and the internal balloons as a unit within the outer balloon for optimal in situ angular positioning of the coil.

27 Claims, 4 Drawing Sheets

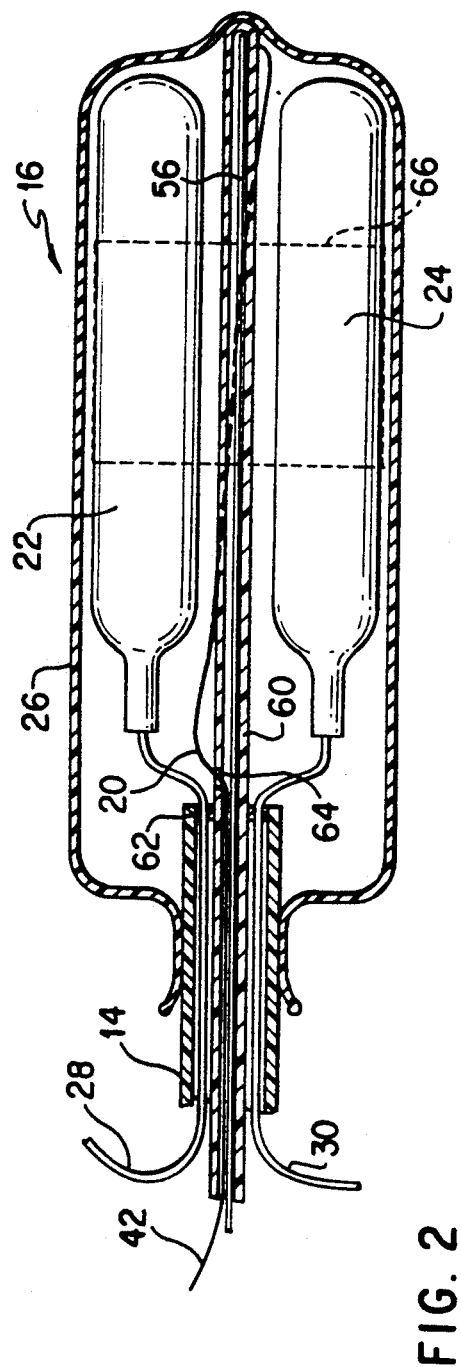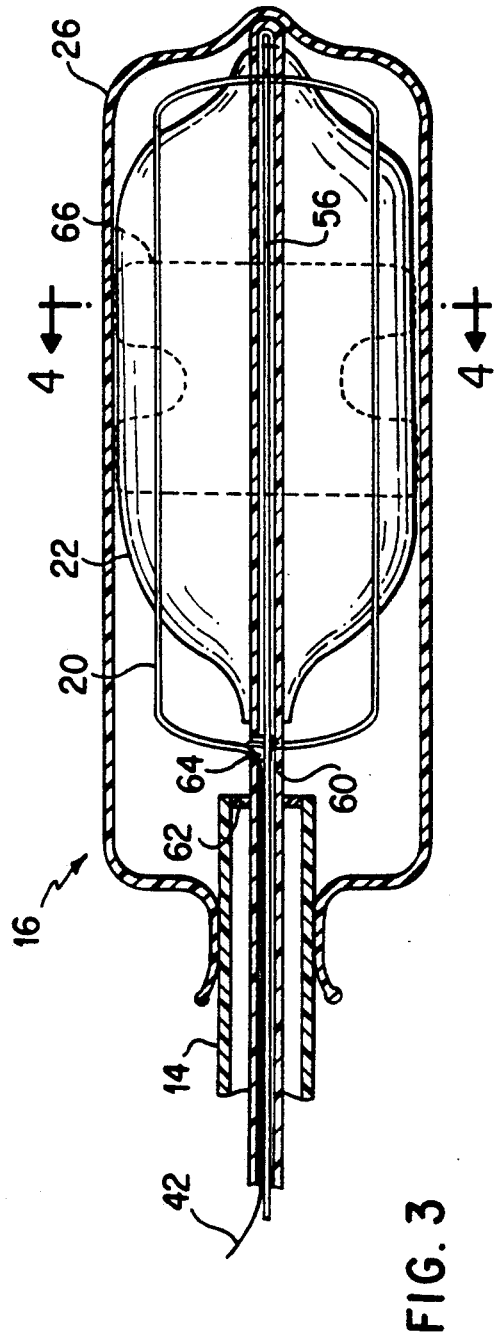

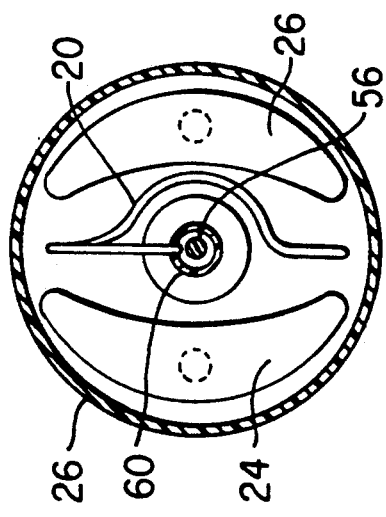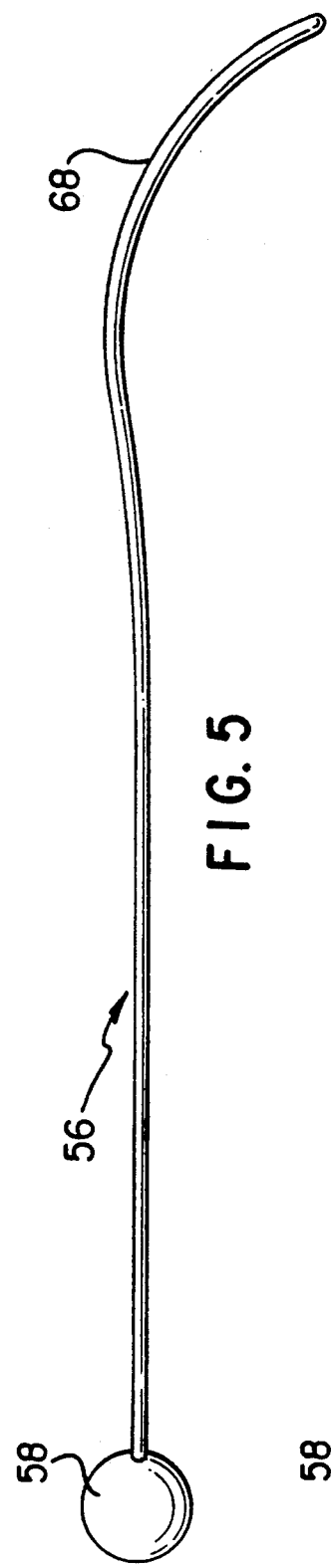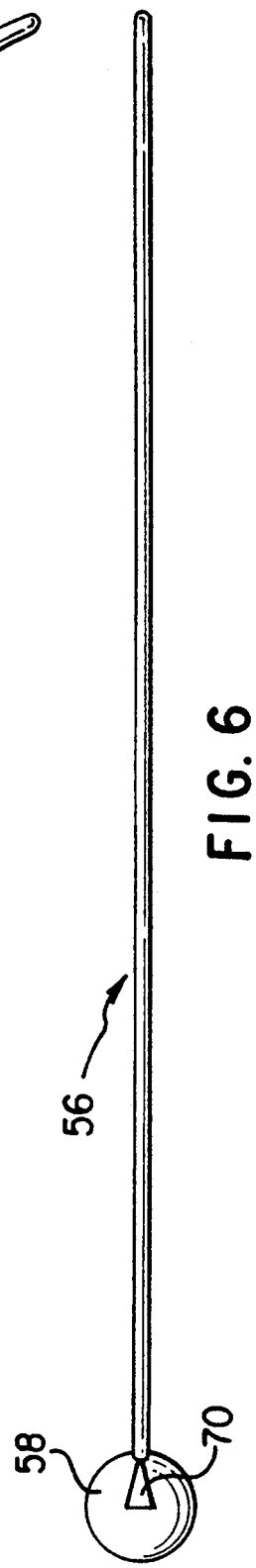

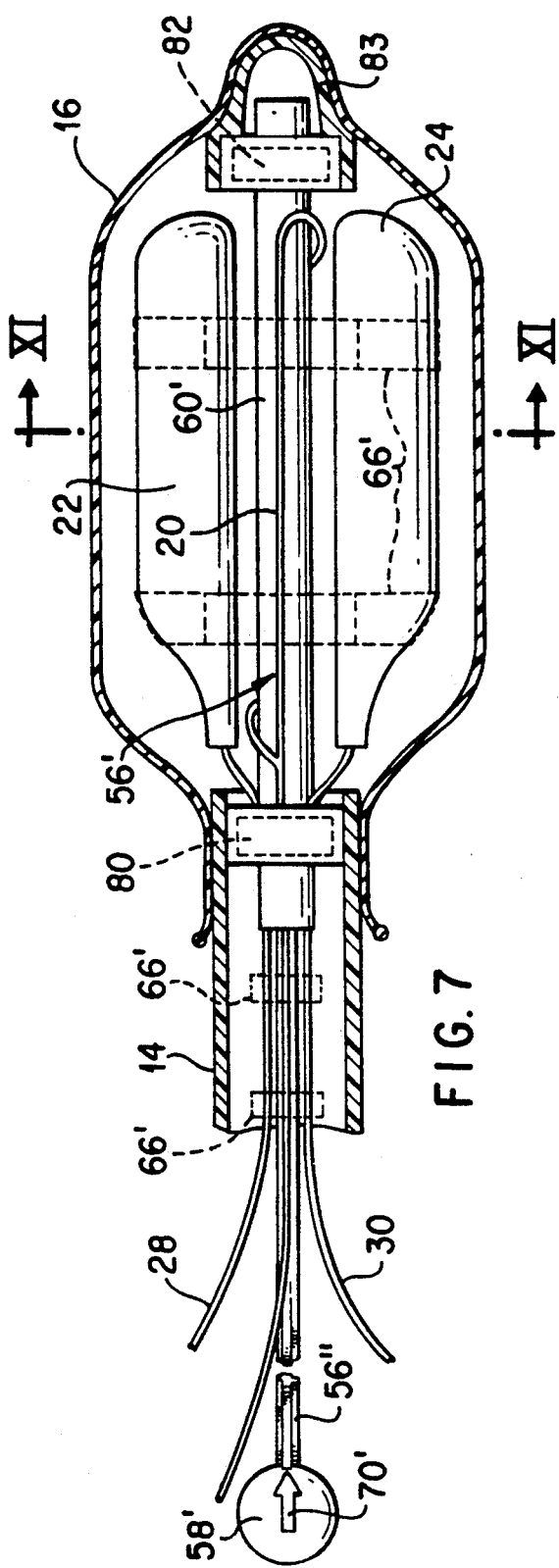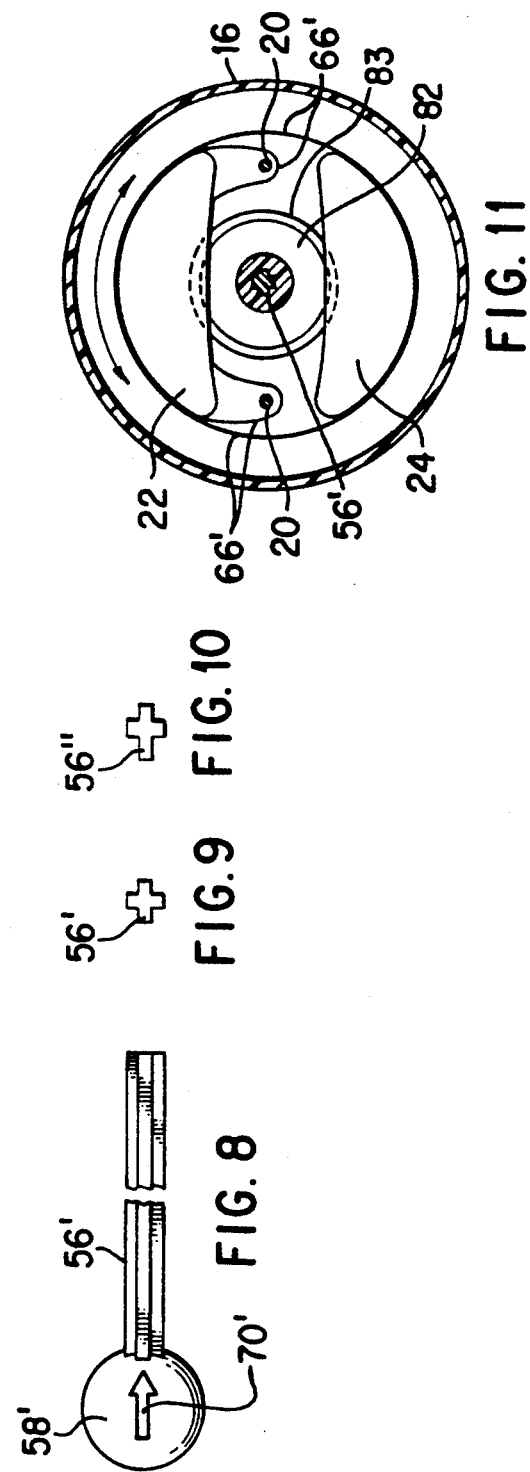

EXTERNALLY MOVEABLE INTRACAVITY PROBE FOR MRI IMAGING AND SPECTROSCOPY

BACKGROUND OF THE INVENTION

This invention relates to a receiving device in the form of an intracavity probe for use in magnetic resonance imaging (MRI) and spectroscopy systems to enhance the imaging performance and spectroscopy sensitivity of such instruments when evaluating anatomical regions small in size relative to the body, and deep within the body, but proximate a location where an insertable pickup probe can be used. Specifically, the present invention relates to an intracavity pickup probe especially useful to image the colon region by rectal introduction, but which may also be useful for inspecting other regions of the body by suitable intracavity insertion.

In the field of MRI systems, also commonly known as NMR imaging systems, external pickup probes are typically used for receiving radio frequency signals from the region of interest. For optimum performance when imaging certain select parts of the body, the pickup probe should be insertable for intracavity use and include a radio frequency receiving coil, to be positioned as close to the region of interest as possible. In addition, the insertable pickup probe should also have a sensitive volume equaling the desired field of view of the region of interest. This allows optimization of the "filling factor" and "coupling coefficient" for the specific MRI system, thereby improving signal to noise ratio in MR imaging.

Furthermore, for optimum sensitivity, the receiving coil should have a loaded coil quality factor (Q) which is as great as possible and should be adjusted to resonate at the exact Larmour frequency of the scanner of the MRI system. It also sometimes is desired that the insertable, intracavity pickup probe be disposable, and hence the cost of the probe should be minimized as much as possible. At the same time, it is important that in reducing the cost of the probe, the ability to impedance match and tune the receiving coil to the scanner of the MRI system not be compromised. Therefore, there is a need to provide a disposable pickup probe at minimal cost for use in a MRI system which is capable of automatic or manual tuning and impedance matching of the receiving coil to the scanner of the MRI system.

SUMMARY OF THE INVENTION

It is an object of the present invention to provide an insertable, intracavity pickup probe capable of being placed in close proximity to a region of interest, particularly in the colon, to improve the quality of a magnetic resonance image or spectrum.

It is a further object of the present invention to provide a insertable MRI pickup probe capable of being manipulated by a clinician during insertion of the probe in a manner accommodating shape variations, curves, bends and the like in a body passage through which the probe is inserted.

Another object of the invention is to provide an insertable MRI pickup probe which when inserted at a site of interest in a body cavity can be manipulated so as to optimize the positioning of the pickup coil in relation to the particular area of interest.

The invention in a specific embodiment relates to an insertable, intracavity pickup probe, and more specifically an intrarectal pickup probe for high sensitivity and high resolution imaging of the colon and associated area. Although the pickup probe is described hereinafter as principally to image or obtain spectra from the area of the colon, it should be understood that the concepts outlined herein are equally appropriate for other regions of interest such as the rectum, vagina, stomach, and mouth. Additionally, the principles described herein may be applied to MRI or NMR application involving the arteries, veins, and other similar regions of the body reachable by an insertable or implantable pickup probe.

The insertable pickup probe of the present invention greatly improves the signal-to-noise ratio of an image or spectrum acquisition over signal pickup devices commonly used with MRI and NMR scanner systems. In addition, the restricted field of view of the probe reduces or eliminates image distortion caused by motion, blood flow, patient breathing, and signal aliasing when conducting an image acquisition using multidimensional fast Fourier transform techniques.

The insertable pickup probe of the present invention comprises a shaft which supports an outer patient interface balloon structure at its distal end. In a specific embodiment, the interface balloon structure contains a receiving coil in the form of a closed substantially planar loop with anterior and posterior faces. Two internal independently inflatable balloons are positioned within the structure on the anterior and posterior sides of the coil, respectively, effectively sandwiching the coil therebetween. The internal balloons have separate inflation tubes which extend through the shaft exiting at the proximal handle end thereof. Each tube has a stopcock or like inflation controller, and each tube is separately connectable to an inflation cuff or the like. The coil is provided with an electrical lead which also extends through the shaft, exiting at the proximal handle end and being provided with a connector for attaching the coil to an interface network to receive signals from the coil.

When the probe is inserted in a body cavity with the balloon structure positioned adjacent an area of interest to be investigated by NMR or MRI imaging, the provision of the separately inflatable internal balloons allows the coil to be more effectively positioned relative to the area of interest by selective and differential inflation. For example, if the area of interest is located on the anterior side of the coil, the posterior-side internal balloon may be inflated to a higher inflation volume than the anterior-side balloon to move the coil toward the anterior.

In accordance with another aspect of the invention, the probe may include steering and locator means to assist a clinician when inserting the probe in a body cavity to accommodate bends or curves in the cavity and to provide a visual indication as to the orientation of the coil. To this end, the probe may include a stiffener tube extending axially through the outer balloon from the proximal end of the shaft, and a removable steering mandrel which can be inserted into the shaft from the proximal end so as to extend through the shaft and stiffener tube substantially up to the distal end of the balloon structure. The mandrel, which may be in the form of a stiff plastic or like rod may have a curved distal end. The effect of the curved end of the mandrel is to provide a type of orbital movement of the balloon structure and coil when the proximal end of the mandrel is axially rotated relative to the shaft during insertion of the probe, useful to provide steering of the probe through curves and the like in body cavity.

According to a further feature of the invention, the mandrel may be used to rotate the coil along with the anterior and posterior balloons within the outer balloon structure. To this end, proximal and distal end rotary bearings are provided within the outer balloon to receive the mandrel, and the coil along with the anterior and posterior balloons are taped together to form, with the mandrel, a rotary unit which can be rotated within the outer balloon by rotation of a knob or the like at the proximal end of the mandrel. Thus, a clinician can angularly position the coil in situ within a patient without rotation of the probe as a whole. The mandrel can be formed with indicator means to display the angular position of the coil.

To provide an indication of the orientation of the coil, the shaft may include a longitudinal sight line or stripe aligned with the coil. Also the mandrel may have a proximal end knob with an arrow or other mark to indicate the direction of the curve of the mandrel to aid in steering.

The above and other objects and advantages of the present invention will become more readily apparent when reference is made to the following description, taken in conjunction with the accompanying drawings.

BRIEF DESCRIPTION OF THE DRAWINGS

FIG. 2 is a cross-sectional plan view of the distal balloon portion of the insertable pickup probe illustrated in FIG. 1.

FIG. 3 is a cross-sectional elevational view of the distal end balloon portion of the probe.

FIG. 4 is a sectional view taken on line 4—4 of FIG. 3.

FIG. 5 is an elevational view of a steering mandrel for the probe.

FIG. 6 is a plan view of the steering mandrel.

FIG. 7 is a view similar to FIG. 2 showing the distal balloon portion of a modified pickup probe according to the invention.

FIG. 8 is an elevational view of a mandrel used in the probe shown in FIG. 7.

FIGS. 9 and 10 are views showing alternative cross-sectional shapes for the mandrel.

FIG. 11 is a cross-section view on line XI—XI of FIG. 7.

DESCRIPTION OF PREFERRED EMBODIMENT

Figure 1:
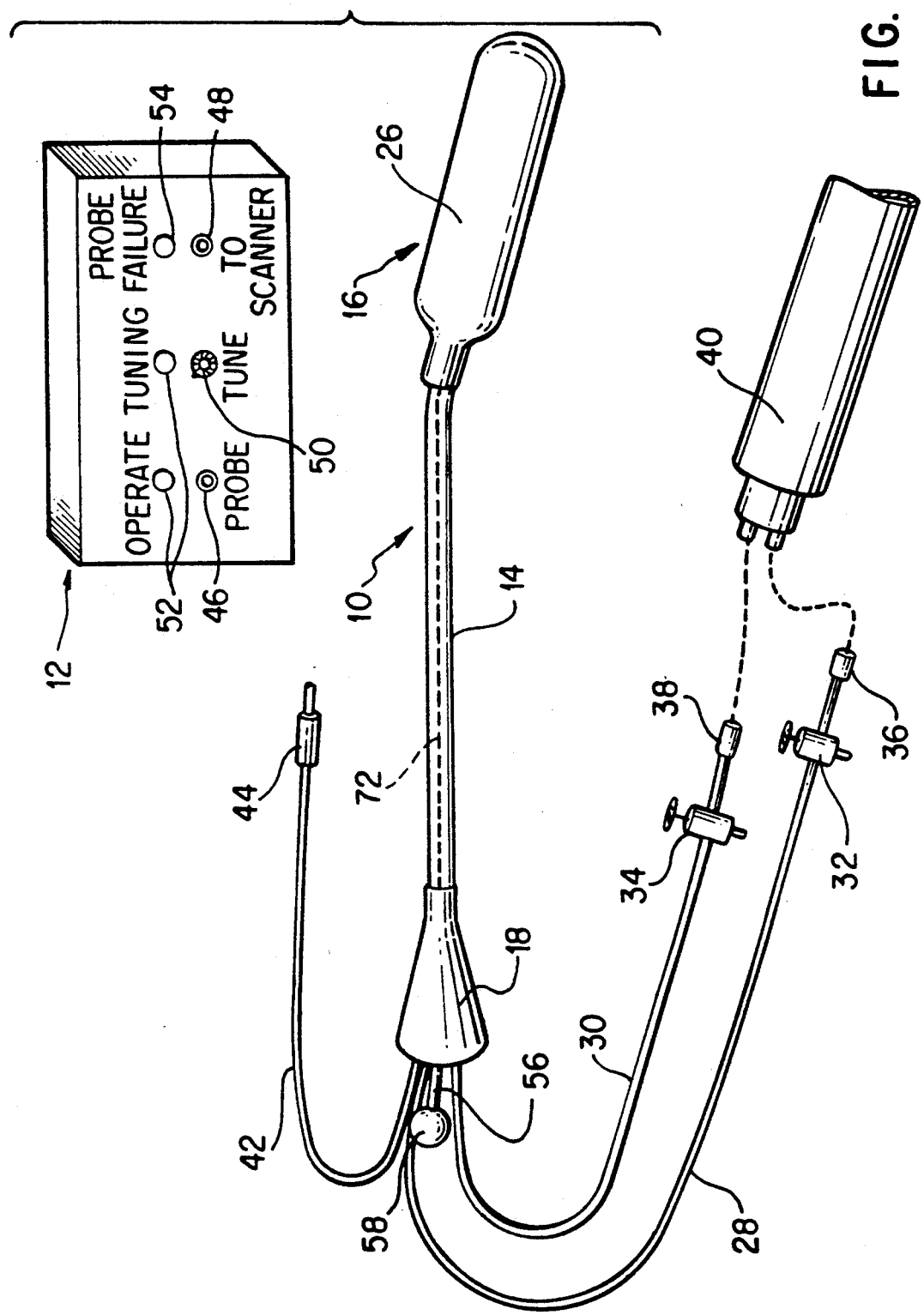
FIG. 1 is a perspective view of an insertable pickup probe in accordance with the present invention and an associated interface network.

Referring first to FIG. 1, an insertable colon pickup probe is shown in an assembled form at 10, and an interface network to which the probe connects is shown at 12. The pickup probe 10 is an MRI or NMR receiving device capable of imaging or gathering spectra from the human colon and surrounding tissue, but may also be used as the transmit coil for RF excitation. The probe 10 is used with the interface network 12 which provides the tuning, impedance matching, and decoupling functions.

The probe 10 includes a shaft 14 which supports a patient interface balloon structure 16 at its distal end and a handle 18 located at the proximal end of the shaft 14. As will be described in more detail later, assembly 16 includes an internal pickup coil 20 and internal anterior and posterior inflation balloons 22 and 24, none of which are shown in FIG. 1. The coil and internal balloons are accommodated, as will be described, in an outer balloon 26. Tubes 28, 30 for inflating the internal balloons extend from the respective balloons through shaft 14 and exit at the proximal end of handle 18. The tubes have respective inflation control stopcocks 32, 34 and connections 36, 38 for attaching same to an inflator device 40 such as a syringe or cuff.

The receiving coil contained within the patient interface balloon structure 16 can be electrically connected to the interface 12 by an insulated interconnecting cable 42 which has a plug 44 at its proximal end for connection to terminal 46 located on the front of the interface network 12.

The interface network 12 also includes a terminal 48 for providing a connection to a MRI scanner. Furthermore, the interface network 12 may include a switch 50 capable of being moved between an operating position and a tuning position or be designed such that it functions fully automatically. To display to the operator the mode of operation, indicator lights 52 or an LED readout are provided on the front of the interface network 12. In addition, a light 54 or an LED readout for indicating the occurrence of a probe failure is provided on the front of the interface network 12.

A removable elongate rod-like steering mandrel 56 extends through the balloon structure 16 and shaft 14. The mandrel has an operating knob 58 at its proximal end.

Referring now to FIGS. 2 to 4, the patient interface balloon structure 16 of the insertable pickup probe 10 is illustrated in more detail. Extending through the shaft 14 and axially through balloon structure 16 is a stiffener tube 60 which is a permanent part of the structure and which may, for example, be supported in shaft 14 by an end plate 62 and a like end plate (not shown) at the proximal end of the shaft. The lead 42 for the pickup coil 20 extends through a lumen of the tube 60 and exits the tube through an aperture 64 adjacent the distal end of shaft 14. Outside of the aperture, lead 42 connects to coil 20 which is in the form of a loop occupying a substantial cross-sectional area of the outer balloon 26.

The internal inflation balloons 22 and 24 embrace the coil 20 on its anterior and posterior sides and also occupy substantial areas of the outer balloon as shown in FIG. 3. The inner balloons are connected at their distal inlet ends to the inflation tubes 28 and 30 which are shown diagrammatically only in FIG. 2. The inflation tubes pass through apertures in end plate 62 and thence through the shaft 14. The inner balloons and coil 20 may be loosely held together as a sandwich-type package by an encircling cuff 66 shown dotted in FIGS. 2 and 3.

The mandrel 56, which is of a stiff plastic or other material, also fits through the lumen of the stiffening tube 60. As shown in FIGS. 5 and 6, the mandrel is linear in plan view but has a J-like bend 68 at its distal end in elevational view. Also, the mandrel operating knob 58 has an indicator mark 70 to show a clinician inserting the probe the alignment of the mandrel. Further, as shown in FIG. 1, the shaft has a lengthwise indicator stripe 72 (shown dotted for convenience only) substantially aligned with the plane of coil 20.

Other constructional details and materials of the various components of the probe are generally known per se and for such details, reference may be made to copending U.S. patent application Ser. No. 07/315,875 filed Jan. 27, 1989 and the contents of which is expressly incorporated herein by reference. Details of the interface network are also shown and described in the copending patent application.

For insertion of the probe by way of a patient's rectum, the internal balloons 22 and 24 would be deflated to minimize the size of the structure 16, it being noted that outer balloon 26 is not inflated. During insertion of the probe, the balloon structure may be given an orbital type twisting movement by rotation of the mandrel, should it be necessary to "steer" the probe along curves or bends in the anal tract or other intercavity passageway.

When the balloon structure is situated at a site to be investigated by MRI or NMR imaging, the probe is manipulated in order to orientate the coil substantially face on to an area of interest. Then, for optimal positioning of the coil relative to said area, the internal balloons ma be differentially inflated with the balloon on that side of the coil which is further from the area of interest being inflated to a higher volume than the balloon which is on the side of the coil facing the area of interest. Differential inflation of the balloons is effected, for example, by opening and closing the respective stopcocks 32 and 34 to allow controlled quantities of air to be delivered to the respective balloons from the inflator device 40. Differential inflation of the balloons as described has the effect of locating the coil in closer proximity to the area of interest than is possible with known forms of inflatable probe devices. Typical inflation volume for the balloons may, for example, be 40 cc in each balloon for a center lumen position of the coil and 10 cc in the anterior balloon and 50 cc in the posterior balloon for an anterior position of the coil.

FIGS. 7-11 show a modified probe structure in which the coil along with the internal balloons may be rotated within the outer balloon so as to allow in situ angular positioning of the coil when in position in a body cavity without having to rotate the probe as a whole when positioned within a patient. Equivalent reference numerals are used to denote parts which are equivalent to those in the previous embodiment.

Thus, in the modified arrangement, a proximal rotary bearing 80 is provided at the distal end of shaft 14 and a similar distal rotary bearing 82 is provided in a bearing support 83 within the outer balloon 16 at its distal end. Stiffener tube 60' is supported for rotation within the bearings 80 and 82, and a relatively stiff mandrel 56' with a proximal end operating knob 58' extends through shaft 14 and tube 60'. The pickup coil 20 and the internal anterior and posterior balloons 22 and 24 are constructed in like manner to the previous embodiment, but in this case they are taped together and also taped to the mandrel by tapes 66' so as to rotate together with the mandrel and stiffener tube as a unit within the outer balloon. The mandrel may have alternative cruciform cross-sectional shapes as shown in FIGS. 9 and 10 received in a correspondingly shaped lumen in the stiffener tube so that rotation of the mandrel by knob 58' when the probe is in situ in a body cavity is effective to rotate the internal balloon assembly within the outer balloon 16. The cruciform shape of the mandrel is also useful for indicating the angular position of the coil relative to the outer balloon along with indicator 70'.

The remainder of the structure of the probe including the handle is similar to that described in connection with FIGS. 1-6.

In all embodiments of the invention the outer balloon 16 may be disposable or covered by a disposable sheath or the like to allow for repeated use of the probe.

While only a preferred embodiment of the invention has been described herein in detail, the invention is not limited thereby and modifications can be made within the scope of the attached claims. Just as a few examples, the mandrel need not be curved, and with an alternate mechanism for aligning the coil, the stiffening tube need not be provided.

We claim:

1. An insertable intracavity probe for use in magnetic resonance imaging with an interface network of a region of interest within a cavity of a patient comprising an elongate shaft having a proximal end and a distal end, a handle on the proximal end of the shaft, and a balloon structure on the distal end of the shaft, the balloon structure including an outer balloon, a pick-up coil in the outer balloon, the coil having an electrical lead extending through the shaft for connecting the coil to the interface network, first and second inflatable inner balloons within the outer balloon, the inner balloons being located on first and second sides of the coil, respectively, sandwiching the coil therebetween, and respective inflation tubes for inflating the inner balloons extending through the shaft.

2. The invention as defined in claim 1 including control means for selectively and individually controlling inflation pressure for the respective inner balloons.

3. The invention as defined in claim 2 wherein the control means includes a stopcock on each of said inflation tubes and connector means for attaching the tubes to an inflation source.

4. The invention as defined in claim 1 which includes a stiffener tube extending from the shaft through the balloon structure.

5. The invention as defined in claim 1 which includes a rod-like mandrel for insertion into the elongate shaft from a proximal end of the handle, the mandrel having a length to extend, when inserted substantially from a distal end of the balloon structure out of the proximal end of the handle.

6. The invention as defined in claim 5 wherein the mandrel has a curved distal end portion for providing orbital twisting movement of the balloon structure on the shaft when the mandrel is rotated in the shaft.

7. The invention as defined in claim 6 wherein the mandrel has a proximal end with a mark for indicating an orientation of the curved distal end portion of the mandrel.

8. The invention as defined in claim 7 wherein the mandrel as a knob at the proximal end and said mark is on the knob.

9. The invention as defined in claim 1 wherein the shaft includes identifying means for indicating an orientation of the coil.

10. The invention as defined in claim 9 wherein the identifying means is a longitudinal stripe on the shaft.

11. A insertable intracavity probe for use in magnetic resonance imaging with an interface network of a region of interest within a cavity of a patient comprising an elongate shaft having a proximal end and a distal end, a handle on the proximal end of the shaft, a balloon structure on the distal end of the shaft including therein a pickup coil having a lead extending through the shaft for connection to the interface network and an elongate rod-like mandrel having a curved distal end within the balloon structure, the mandrel being insertable within the shaft from a proximal end of the handle, and being for providing guidance and positioning of the balloon structure during insertion into the cavity.

12. The invention as defined in claim 11 which includes a stiffener tube extending from the shaft through the balloon structure and wherein the mandrel fits in a lumen in the stiffener tube.

13. The invention as defined in claim 12 wherein the stiffener tube is rotatably mounted in distal and proximal bearings in the balloon structure whereby rotation of the mandrel effects rotation of the stiffener tube and coil.

14. The invention as defined in claim 13 wherein the coil is embraced by first and second inflatable inner balloons for providing selective positioning of the coil.

15. The invention as defined in claim 11 wherein the mandrel has a proximal end provided with a knob and a mark for indicating orientation of the mandrel in the shaft.

16. An insertable intracavity probe for use in magnetic resonance imaging with an interface network of a region of interest within a cavity of a patient comprising an elongate shaft having a longitudinal axis, a proximal end and a distal end, a handle on the proximal end of the shaft, a balloon on the distal end of the shaft including therein a pickup coil having a lead extending through the shaft for connection to the interface network, a rotatable stiffener tube extending from the shaft through the balloon, bearing means rotatably mounting the stiffener tube within the balloon, an elongate mandrel extending substantially coaxially through the handle, the shaft and a lumen in the stiffener tube whereby rotation of the mandrel effects rotation of the stiffener tube, the mandrel having a proximal end portion extending outwardly from the handle, and attachment means within the balloon securing the coil to the stiffener tube and mandrel for rotation therewith whereby the coil can be angularly rotated and positioned within the balloon by rotation of said proximal end portion of the mandrel.

17. The invention as defined in claim 16 including first and second inflatable inner balloons within the balloon on the shaft, the inner balloons being located on first and second sides of the coil, respectively, sandwiching the coil therebetween, and respective inflation tubes for inflating the inner balloons extending through the shaft wherein the attachment means also secures the inner balloons to the stiffener tube and mandrel for rotation therewith.

18. The invention as defined in claim 16 wherein the bearing means includes a proximal rotary bearing at a proximal end of the balloon, and a distal rotary bearing at a distal end of the balloon.

19. The invention as defined in claim 16 wherein the mandrel includes indicator means for indicating angular orientation of the coil within the balloon.

20. The invention as defined in claim 19 wherein the mandrel has a cross-sectional shape for indicating the angular orientation of the coil within the balloon.

21. The invention as defined in claim 20 wherein the mandrel has a cruciform cross-section.

22. A method of magnetic resonance imaging of a region of interest within a cavity of a patient including the steps of inserting a pickup probe into said cavity, the probe having a distal end balloon structure including a pickup coil and first and second internal inflatable balloons within said structure embracing the coil on opposite sides of the coil, respectively, positioning the balloon structure proximate said region of interest, providing selective and independent inflation of the internal balloons to influence positioning of the coil within said structure so as to optimally position the coil in relation to said region of interest, and using the coil for said imaging.

23. A method as defined in claim 22 which further includes rotating the coil and inner balloons with said balloon structure to obtain optimal positioning of the coil.

24. In a method of magnetic resonance imaging of a region of interest within a cavity of a patient using a pcikup probe having an elonage shaft with a balloon structure at a distal end thereof including a pickup coil therein an an elongate mandrel having a curved distal end inserted into the shaft and extending into the balloon structure, the improvement which comprises manipulating the balloon structure by rotation of the elongate mandrel about a lengthwise axis of the shaft to assist in, positioning of the probe, and using the pickup coil for said imaging.

25. The method defined in claim 24 wherein the method further comprises providing orbital movement of the balloon structure about the shaft by rotation of the mandrel.

26. A method of magnetic resonance imaging a region of interest within a cavity of a patient including the steps of inserting a pickup probe into said cavity, the probe having a distal end balloon structure including a pickup coil therein, positioning the balloon structure proximate said region of interest, selectively rotating the coil within said balloon structure to optimally position the coil with respect to said region of interest and using the coil for said imaging.

27. A method as defined in claim 26 further including a step of influencing the coil laterally within the balloon structure to obtain optimum positioning of the coil in relation to said region of interest.

* * * * *